United States Patent
Poolman

(10) Patent No.: US 8,916,173 B2
(45) Date of Patent: Dec. 23, 2014

(54) ACELLULAR PERTUSSIS VACCINE

(71) Applicant: Crucell Holland B.V., Leiden (NL)

(72) Inventor: Jan Theunis Poolman, Haarlem (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 14/199,879

(22) Filed: Mar. 6, 2014

(65) Prior Publication Data
US 2014/0255446 A1    Sep. 11, 2014

Related U.S. Application Data

(60) Provisional application No. 61/774,993, filed on Mar. 8, 2013.

(30) Foreign Application Priority Data

May 27, 2013  (EP) .................................. 13169328

(51) Int. Cl.
- A61K 39/295  (2006.01)
- A61K 39/10   (2006.01)
- A61K 39/13   (2006.01)
- A61K 39/29   (2006.01)

(52) U.S. Cl.
USPC .................. 424/203.1; 424/201.1; 424/254.1; 424/240.1; 424/278.1; 424/236.1

(58) Field of Classification Search
None
See application file for complete search history.

(56) References Cited

U.S. PATENT DOCUMENTS

| | | | |
|---|---|---|---|
| 4,372,945 A | 2/1983 | Likhite | |
| 4,474,757 A | 10/1984 | Arnon et al. | |
| 4,525,349 A | 6/1985 | Montagnon et al. | |
| 4,673,574 A | 6/1987 | Anderson | |
| 4,705,868 A | 11/1987 | Deschler et al. | |
| 4,709,017 A | 11/1987 | Collier et al. | |
| 4,784,589 A | 11/1988 | Robinson et al. | |
| 5,057,540 A | 10/1991 | Kensil et al. | |
| 5,085,862 A | 2/1992 | Klein et al. | |
| 5,101,014 A | 3/1992 | Burns et al. | |
| 5,276,142 A | 1/1994 | Gotto | |
| 5,601,827 A | 2/1997 | Collier et al. | |
| 5,843,711 A | 12/1998 | Collier et al. | |
| 5,917,017 A | 6/1999 | Collier et al. | |
| 6,013,264 A | 1/2000 | Petre et al. | |
| 6,333,036 B1 | 12/2001 | Arminjon et al. | |
| 6,444,211 B2 | 9/2002 | Jackson et al. | |
| 6,475,754 B1 | 11/2002 | Bemis et al. | |
| 7,144,576 B1 | 12/2006 | Burnette, III | |
| 7,427,404 B1 | 9/2008 | Pizza et al. | |
| 7,666,436 B1 | 2/2010 | Pizza et al. | |

FOREIGN PATENT DOCUMENTS

| | | |
|---|---|---|
| EP | 0161188 | 11/1985 |
| EP | 0162639 | 11/1985 |
| EP | 0208375 | 1/1987 |
| EP | 0209281 | 1/1987 |
| EP | 0226846 | 7/1987 |
| EP | 0275689 | 7/1988 |
| EP | 0299108 | 1/1989 |
| EP | 0306318 | 3/1989 |
| EP | 0322533 | 7/1989 |
| EP | 0336736 | 10/1989 |
| EP | 0396964 | 11/1990 |
| EP | 0427462 | 5/1991 |
| EP | 0477508 | 4/1992 |
| EP | 0484621 | 5/1992 |
| EP | 0555894 | 8/1993 |
| EP | 1946769 | 7/2008 |
| WO | 9003184 | 4/1990 |
| WO | 9004641 | 5/1990 |
| WO | 9013313 | 11/1990 |
| WO | 9014837 | 12/1990 |
| WO | 9015871 | 12/1990 |
| WO | 9112020 | 8/1991 |
| WO | 9115505 | 10/1991 |
| WO | 9324148 | 12/1993 |
| WO | 9508348 | 3/1995 |
| WO | 9611711 | 4/1996 |
| WO | 9634023 | 10/1996 |
| WO | 9634623 | 11/1996 |
| WO | 9634883 | 11/1996 |
| WO | 9800167 | 1/1998 |
| WO | 9819702 | 5/1998 |
| WO | 9858668 | 12/1998 |
| WO | 9948525 | 9/1999 |
| WO | 0207764 | 1/2002 |
| WO | 2004004762 | 1/2004 |
| WO | 2004110480 | 12/2004 |
| WO | 2005002620 | 1/2005 |
| WO | 2007054820 | 5/2007 |
| WO | 2008028956 | 3/2008 |
| WO | 2010046935 | 4/2010 |
| WO | 2011006823 | 1/2011 |
| WO | 2012117377 | 9/2012 |

OTHER PUBLICATIONS

Bouchez et al. Vaccine 27 (2009) 6034-6041.*
International Search Report; PCT/EP2014/054379 dated Apr. 10, 2014.
Written Opinion; PCT?EP2014-054379 dated Apr. 10, 2014 5 pgs.
European Search Report; EP13169328 dated Oct. 29, 2013; 6 pgs.
Halperin et al.; Safety and Immunogenicity of a Five-Component Acellular Pertussis Vaccine With Varying Antigen Quantities; Arch Pediatr Adolesc Med/ vol. 148, Nov. 1994; pp. 1220-1224.
Langley et al.; An adolescent-adult formulation tetanus and diptheria toxoids absorbed combined with acellular pertussis vaccine has comparable immunogenicity but less reactogenicity in children 4-6 years of age than a pediatric formulation accellular pertussis vaccine and diptheria and tetanus toxoids absorbed combined with inactivated poliomyelitis vaccine; Vaccine 25 (2007) 1121-1125.

(Continued)

Primary Examiner — Oluwatosin Ogunbiyi
(74) Attorney, Agent, or Firm — TraskBritt, P.C.

(57) ABSTRACT

Described are acellular *pertussis* (aP) vaccine compositions comprising *Bordetella pertussis* antigens *pertussis* toxoid (PT), filamentous hemagglutinin (FHA), and fimbriae types 2 and 3 (FIM), and optionally pertactin (PRN), wherein FIM is present in an amount of 12-100 μg per human dose.

25 Claims, 3 Drawing Sheets

(56) References Cited

OTHER PUBLICATIONS

Figure 1:
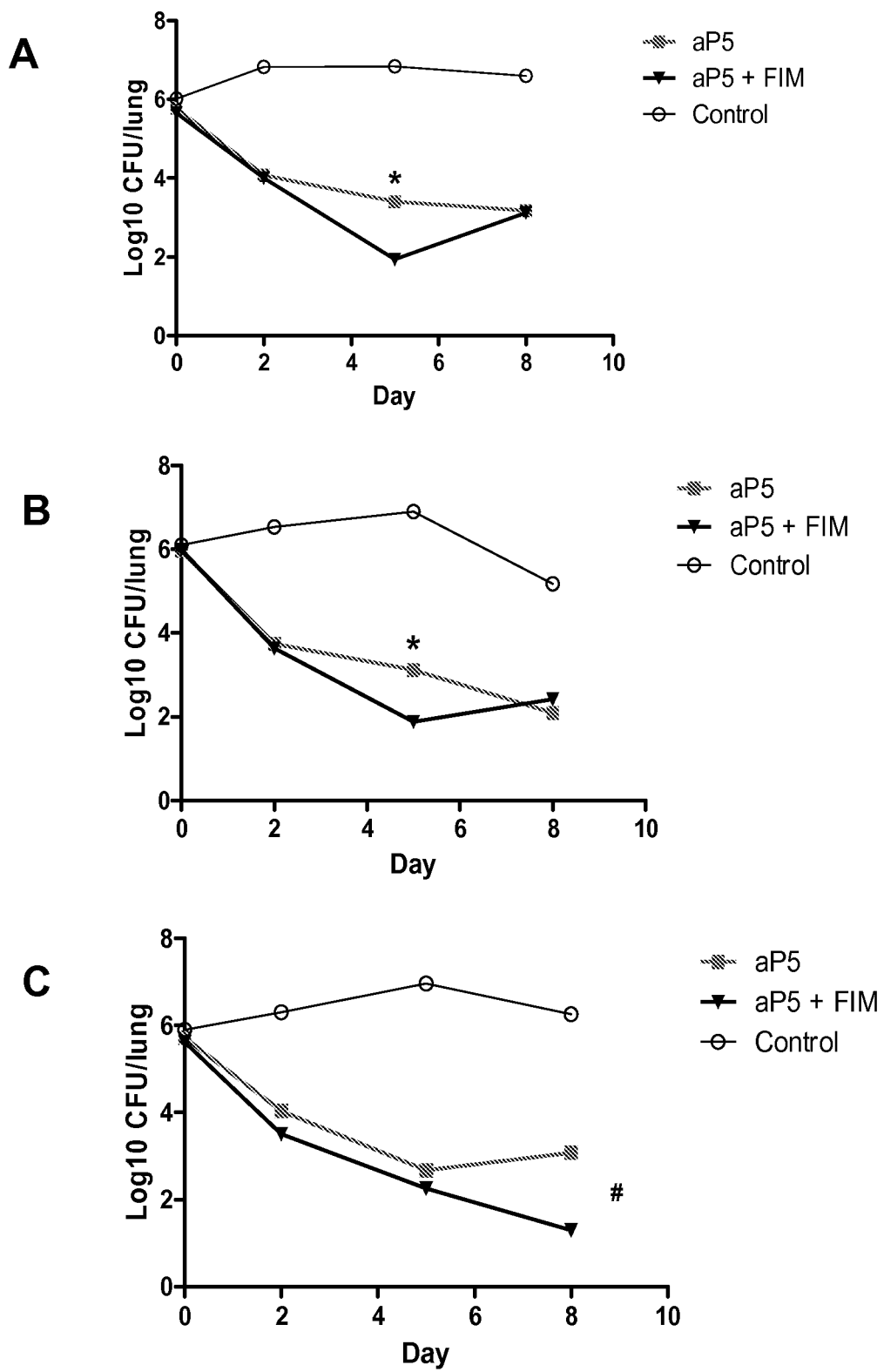
Figure 2:
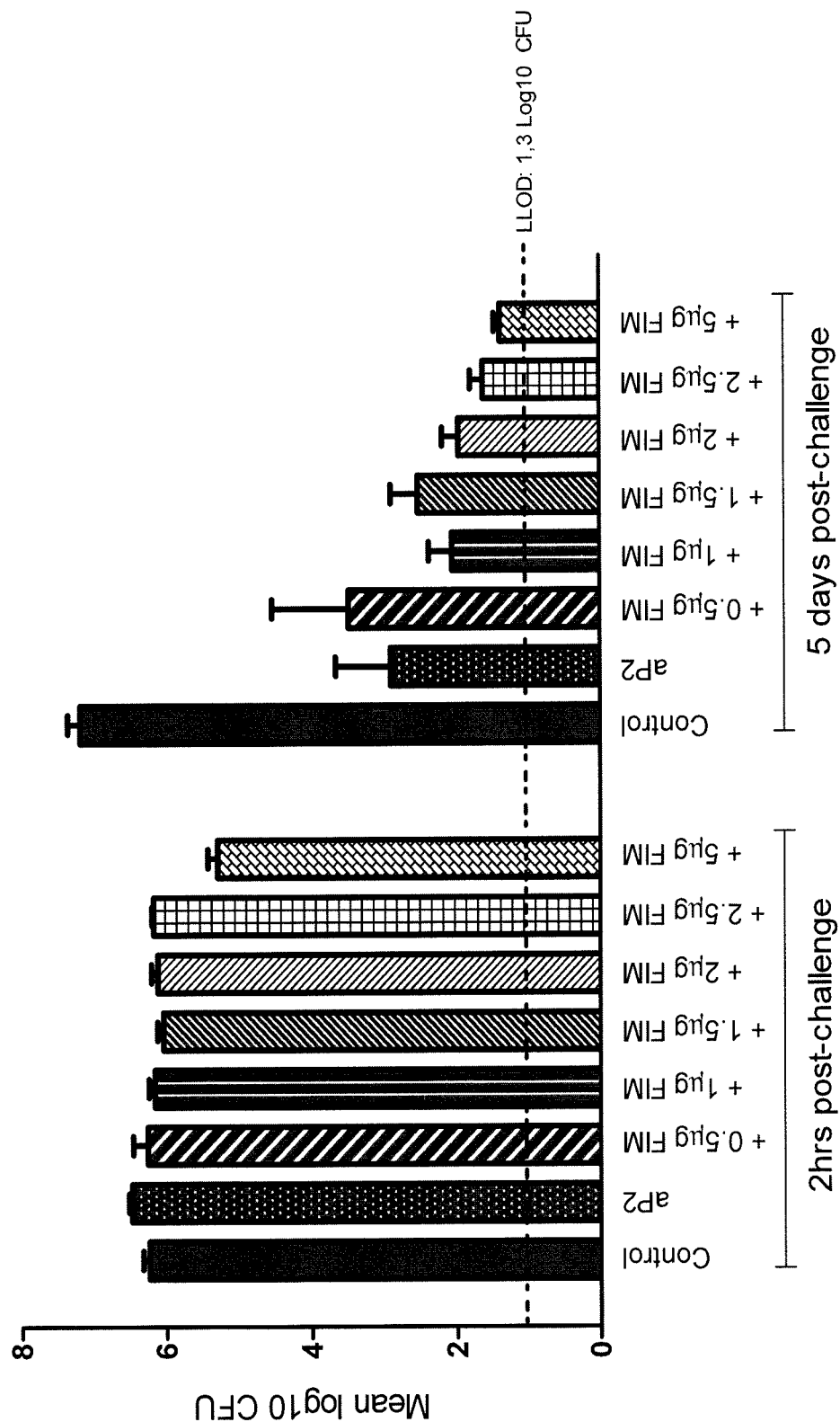
Figure 3:
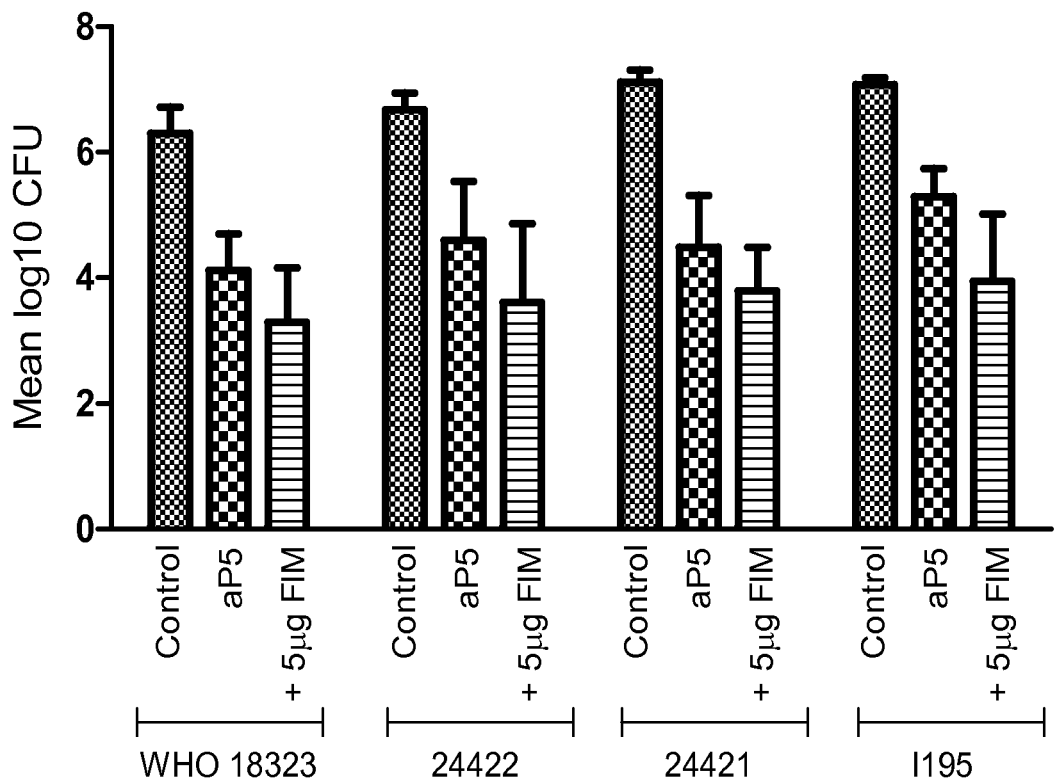

Marzouqi et al.; Development of improved vaccines against whooping cough; Human Vaccines 6:7, 543-553; Jul. 2010.

Pichichero et al.; Safety and immunogenicity of Six Acellular Pertussis Vaccines and One Whole-Cell Pertussis Vaccine Given as a Fifth Dose in Four- to Six-Year-Old Children; Pediatrics; vol. 105, No. 1; Jan. 2000; 9 pgs.

Queenan et al; Pertactin-Negative Variants of *Bordetella pertussis* in the United States; N Engl J. Med 368;6; Feb. 7, 2013; 583-584.

Warfel et al.; Acellular pertussis vaccines protect against disease but fail to prevent infection and transmission in nonhuman primate model; PNAS; Jan. 14, 2014; vol. 111; No. 2; 787-792.

Xu et al.; Production and characterization of recombinant pertactin, fimbriae 2 and fimbriae 3 from *Bordetella pertussis*; BMC Microbiology; Dec. 29, 2009; 8 pgs.
Hegerle et al., *Bordetella pertussis* and pertactin-deficient clinical isolates: lessons for pertussis vaccines, Expert Rev. Vaccines, 2014, pp. 1-12.
Queenan et al., Pertactin-Negative Variants of *Bordetella pertussis* in the United States, N. Engl. J. Med., Feb. 7, 2013, pp. 583-584, vol. 368, No. 6.
Hegerle, Evolution of *Bordetella pertussis* and *Bordetella parapertussis* under acellular pertussis vaccine pressure, Doctorate Dissertation, Mar. 18, 2014.
Hegerle et al., Pertactin deficient *Bordetella pertussis* present a better fitness in mice immunized with an acellular pertussis vaccine, Vaccine, 2014, Article in Press, 4 pages.

* cited by examiner

ACELLULAR PERTUSSIS VACCINE

CROSS-REFERENCE TO RELATED APPLICATION(S)

This application claims the benefit under 35 U.S.C. §119(e) of U.S. Patent Application Ser. No. 61/774,993 filed on Mar. 8, 2013 and under 35 U.S.C. §119 to European Patent Application Serial No. 13 169 328.5 filed May 27, 2013, the contents of the entirety of each of which are incorporated herein by this reference.

TECHNICAL FIELD

The disclosure relates to the field of health care. More particularly, it relates to the field of acellular *pertussis* vaccines.

BACKGROUND

*Bordetella pertussis* is the causative agent of whooping cough. Introduction of killed whole-cell *B. pertussis* (wP) vaccines in the 1940s has been successful in reducing the morbidity and mortality due to whooping cough in children and infants (on the World Wide Web at cdc.gov/vaccines/pubs/pinkbook/downloads/pert.pdf; Bisgard, K. M. on the World Wide Web at cdc.gov/vaccines/pubs/pertussisguide/downloads/chapter1.pdf. 2000; Edwards, K. M. & Decker, M. D. Pertussis vaccines. In *Vaccines* (eds. Plotkin, S. A., Orenstein, W. A. & Offit, P. A.) Elsevier Health Sciences, 2008. 467-517; this textbook is hereinafter referred to as "*Vaccines*, Plotkin 2008"). Nevertheless, worldwide, *pertussis* remains an important problem in children. Estimates from the WHO suggest that in 2008 about 16 million cases of *pertussis* occurred, and that about 195,000 children died from this disease.

Since the 1990s wP vaccines have been replaced by acellular *pertussis* (aP) vaccines in most high-income and more recently also in some middle-income countries. Acellular *pertussis* vaccines induce relatively fewer side-effects compared to wP vaccines that are associated with a high risk for fever (>38° C.), reactogenicity at the injection site and, although to a lesser extent, convulsions and hypotonic-hyporesponsive episodes [Zhang, *Cochrane Database Syst Rev* 2011).

One to two decades after introducing aP vaccines, a rise in *pertussis* notifications in adolescents and adults has been reported by several countries, including the US, UK, Australia, Norway and the Netherlands. Possible explanations include improved diagnostics and surveillance, adaptation of circulating *B. pertussis* strains to vaccines, and/or increased waning immunity associated with aP vaccines (Tanaka, *Jama* 2003, 290: 2968-2975; Satoh, *Comp Immunol Microbiol Infect Dis* 2010, 33: e81-88; Zepp, *Lancet Infect Dis* 2011; De Greeff, *PLoS One* 2010: e14183; Tan, *Pediatr Infect Dis J* 2005, 24(5 Suppl): S10-18).

Currently, all licensed aP vaccines consist of minimal one, but mostly multiple, up to a maximum of five (detoxified) *B. pertussis* virulence factors. All aP vaccines contain *pertussis* toxoid (PT). Multicomponent aP vaccines at least include PT and the *B. pertussis* surface adhesin filamentous hemagglutinin (FHA). With increasing valency further one or more of the adhesins pertactin (PRN) and fimbriae type 2 and type 3 (FIM2 and FIM 3, together referred to as FIM or FIM2/3 herein) are present (Edwards, In: *Vaccines*, Plotkin, 2008. 467-517).

WO 96/34883 describes doses of 1-10 µg of FIM per human dose, with doses of 10 and 5 µg per human dose in an aP vaccine exemplified, while only doses of 5 µg per human dose were actually tested, and the tested vaccines were considered efficacious.

It is generally believed that aP5 vaccines (acellular *pertussis* vaccines with the five components PT, FHA, PRN, FIM2/3; DTaP5 are aP5 vaccines further comprising tetanus toxoid and *diphtheria* toxoid) are the most effective aP vaccines currently available. The individual amounts of the aP components present in commercially available registered aP5 vaccines are (in microgram per human dose): 2.5-20 for PT, 5-20 for FHA, 3 for PRN and 5 for FIM.

In several of the acellular *pertussis* vaccine efficacy trials conducted in Europe in the mid-1990s, efforts were made to determine immune correlates of protection for the individual aP vaccine components. Using data from the Swedish DTaP5 (PT+FHA+PRN+FIM2/3) trial a statistically significant correlation between clinical protection and the presence in pre-exposure sera of IgG antibodies against PRN, FIM2 and PT, but not to FHA, were demonstrated (Storsaeter, *Vaccine* 1998, 16: 1907-1916). FIM3 appears to be a nonprotective component within DTaP5 (Poolman, *Expert Reviews Vaccines* 2007, 6: 47-56).

Sera collected from subjects from a vaccine trial in Germany allowed estimation of the specific levels of antibody to PT, FHA, PRN and FIM2 that correlated with protection, which showed that only antibodies against PRN, and PT were significantly associated with protection (Stehr, 1998, *Pediatrics* 101: 1-11; Cherry, 1998, *Vaccine* 16: 1901-1906). In addition, pre-clinical studies have shown that the addition of PRN enhances the level of protection conferred by vaccines that contain PT and FHA in a murine intranasal infection model (Guiso, 1999, *Vaccine* 17: 2366-2376; DeNoel, 2005, *Vaccine* 23: 5333-5341) and that antibodies to PRN were crucial for opsonophagocytosis of *B. pertussis* (Hellwig, 2003, *JID* 188: 738-742). Together these data indicate that PT and PRN are the main protective antigens in current acellular *pertussis* vaccines.

As part of a prospective aP vaccine efficacy trial, protective IgG against PT, FHA, PRN and FIM2/3 was measured in consecutive serum samples obtained from participants over an 18-month period. Over the 18-months the percent decay in IgG against PT was strongest (73% reduction in geometric mean IgG titer) and was significantly higher than the percent reduction in antibodies against PRN, FHA and FIM. In contrast, IgG antibody to PRN had the lowest decay rate (56% reduction in geometric mean IgG titer) (Le, 2004, *JID*, 190: 535-544).

Combining the two observations that 1) PT and PRN are the main protective antigens in aP vaccines and 2) that antibodies to PT have a significantly higher decay rate than antibodies to PRN, highlights that anti-PRN antibodies are crucial in providing aP-mediated long-term protection against *B. pertussis* infection.

However, an emergence of *B. pertussis* strains not expressing PRN has been observed in the last few years around the world, for example, in France, Japan, the Netherlands, the USA, Finland, Norway and Sweden (Bouchez, 2009, *Vaccine* 27: 6034-41; Hegerle, 2012, *Clin. Microbiol. Infect.* 18: E340-346; Otsuka, 2012, *PLoS One* 7: e31985; Advani, 2013, *J. Clin. Micro* 51: 422-428). A recent study in the US showed that 11 out of 12 isolates of *B. pertussis* cultured from specimens from children hospitalized in Philadelphia during 2011 and 2012 were in fact PRN-negative (Queenan, 2013, *N Engl J Med.* 368: 583-4). Whether this strain adaptation is primarily vaccine-driven is currently not known. It is possible that these PRN-negative strains can escape vaccine induced immunity, especially when anti-PT titers have declined, and that this has contributed to the observed increase in *B. pertussis* disease.

The currently licensed and marketed aP vaccines thus appear insufficiently efficacious, especially against the newly emerging PRN-negative strains.

SUMMARY OF THE DISCLOSURE

We have surprisingly found that aP vaccines comprising a high dose of FIM2/3 shows a significantly improved protection against PRN-negative *B. pertussis* strains. The disclosure provides an acellular *pertussis* (aP) vaccine composition comprising *B. pertussis* antigens *pertussis* toxoid (PT), filamentous hemagglutinin (FHA), and fimbriae types 2 and 3 (FIM), and optionally pertactin (PRN), wherein FIM is present in an amount of 12-100 μg per human dose.

In certain embodiments, FIM is present in an amount of 15-80, 15-60, 20-60, or 12-50, 15-50, 20-50, 20-30, 20-25, or 12-30, or 12-25, or about 13, 14, 15, 16, 17, 18, 19, 20, 21, 22, 23, 24, or 25 μg per human dose.

In certain embodiments, the aP vaccines/immunogenic compositions of the disclosure comprise pertactin (PRN).

In certain embodiments, PT is genetically detoxified.

In certain embodiments, the compositions of the disclosure further comprise antigens from one or more pathogens other than *B. pertussis*.

In certain embodiments thereof, the compositions comprise one or more of: a) tetanus toxoid; b) *diphtheria* toxoid; c) *Haemophilus influenzae* type-b (Hib) oligosaccharide or polysaccharide conjugate; d) hepatitis B virus surface antigen (HBSAg); and e) inactivated polio virus (IPV). In certain embodiments, the compostions of the disclosure comprise an acellular *pertussis* vaccine composition, according to the disclosure, tetanus toxoid and *diphtheria* toxoid.

In certain embodiments, the compositions hereof further comprise an adjuvant. In certain embodiments, the adjuvant comprises an aluminum salt, such as aluminum phosphate, aluminum hydroxide, or both aluminum phosphate and aluminum hydroxide.

Also provided is a method for inducing an immune response in, or for vaccinating, a subject against *B. pertussis*, comprising administering to the subject a composition hereof.

Also provided is a method for protecting a subject from whooping cough that is caused by infection with a PRN-negative strain of *B. pertussis*, comprising administering to the subject a composition hereof.

Also provided are compositions for use in inducing an immune response in, or for vaccinating, a subject against *B. pertussis* by administering the composition to the subject. Also provided are the compositions for preparing a medicament for inducing an immune response in, or for vaccinating, a subject against *B. pertussis* by administering the composition to the subject. In certain embodiments, the *B. pertussis* against which an immune response is desired comprises a PRN-negative strain.

Also provided is a method for vaccinating a human subject against *Bordetella pertussis*, optionally a PRN-negative strain of *Bordetella pertussis*, comprising administering to the subject the following *Bordetella pertussis* antigens: *pertussis* toxoid (PT), filamentous hemagglutinin (FHA), and fimbriae types 2 and 3 (FIM), and optionally pertactin (PRN), wherein FIM is administered in an amount of 12-100 μg.

The aP immunogenic compositions disclosed herein have improved efficacy in particular against such PRN-negative *B. pertussis* strains.

BRIEF DESCRIPTION OF THE FIGURES

FIG. 1: Mean log 10 CFU of *B. pertussis* per lung on day 0, 2, 5 and 8 post intranasal challenge in mice vaccinated with a DTaP5 vaccine (aP5) or aP5+FIM. Mice were vaccinated at 4 and 7 weeks of age and challenged intranasally at 9 weeks with different strains of *B. pertussis*: WHO 18323 (FIG. 1A), a clinical PRN-negative isolate PRN-STOP (FIG. 1B) and a clinical PRN-negative isolate PRN-IS (FIG. 1C).

* $p<0.05$ comparing the mean log 10 CFU counts after vaccination with aP5 and aP5+FIM on each specific time point, using Wilcoxon Exact Test.

$p<0.01$ comparing the log 10 CFU response-time profile from day 0 to day 8, after vaccination with aP5 and aP5+FIM using Analysis of Covariance.

FIG. 2: Mean Log 10 CFU counts from the lung in mice challenged with PRN-negative *B. pertussis* strain I195 at week 9 after vaccination with aP2 vaccine at 1⁄10 human dose with the addition of an increasing amount of FIM at 4 and 7 weeks of age. For details see example 2.

FIG. 3: Mean Log 10 CFU counts from the lung in mice 5 days post challenge with 4 strains of *B. pertussis* at week 9 after vaccination with aP5 vaccine at 1⁄10 human dose with or without the addition of 5 μg FIM at 4 and 7 weeks of age. For details see example 3.

DETAILED DESCRIPTION

Disclosed are compositions comprising detoxified *Bordetella pertussis* virulence factors, in particular *pertussis* toxoid (PT), filamentous hemagglutinin (FHA), and fimbriae types 2 and 3 (FIM), and optionally pertactin (PRN), wherein FIM is present in an amount of 12-100 μg per human dose. Such compositions can be used as an acellular *Pertussis* (aP) vaccine, and are demonstrated herein to be surprisingly more efficacious than a currently available best-in-class aP5 vaccine.

In particular, the increased dose of FIM as compared to the previously described and recommended dosage for this component results in improved vaccine efficacy against newly emerging PRN-negative strains of *B. pertussis*, as compared to a marketed aP5 vaccine and other marketed aP vaccines. This is highly surprising, as the prior art does not provide any suggestion to increase the amounts of FIM per human dose over the recommended 5 μg, and the art provides actually suggestions that increasing the amount of this component does not lead to improved efficacy.

The effect of an increased dosage of FIM in vaccines has, for instance, been investigated in humans and animal models. In 17-19 month old infants it was shown that there were no differences in the frequency of adverse reactions, antibody titers or in mean fold titer rise post-immunization between two 5-component aP vaccines with either 10 μg of PT, 5 μg of FHA, 3 μg of PRN and 5 μg of FIM2/3 or including double the amount of all these antigens (Halperin, *Arch Pedi Adol Med* 1994, 148: 1220-1224).

In animal models, it was found that there were no differences in body weight, spleen weight, peripheral leukocyte counts and clearance of *B. pertussis* from the lungs, when mice were vaccinated with three kinds of *pertussis* vaccines that contained different amounts of FIM (Morokuma, *Devel Biol Stand* 1991, 73: 223-232).

Another study showed that there was no difference in IgG antibody level between mice receiving either a high dose (20 µg) or a low dose (4 µg) of recombinant FIM2 or FIM3. Seven days post intranasal challenge there was no difference in bacterial loads in the lung of control mice, mice vaccinated with FIM2 or mice vaccinated with FIM3 (Xu, *BMC Microbiology* 2009, 9:274-281).

Our finding of increased efficacy of vaccination using a high dose of FIM in the mouse nasopharyngeal challenge model is therefore highly surprising.

Thus, no indications or suggestions are believed to exist in the prior art that increasing the amount of FIM in aP vaccines over the usual amount would result in improved efficacy against newly emerging PRN-negative mutant strains.

A "human dose" as used herein (sometimes referred to as a "single human dose"), means an amount of vaccine that is administered to a human in a single administration. Typically, this amount is present in a volume of 0.1-2 ml, e.g., 0.2-1 ml, typically 0.5 ml. The indicated amounts may, thus, for instance, be present at a concentration of micrograms per 0.5 ml bulk vaccine. In certain embodiments a (single) human dose thus equals 0.5 ml.

The components of several aP vaccines that are or have been marketed are described in Tables 21-3 and 21-4 of "Vaccines. 5th edition. S. Plotkin, W. Orenstein, P. Offit, 2008, Section 2, Chapter 21 *"Pertussis* vaccines," K. M. Edwards & M. D. Decker. p. 467-517, incorporated by reference herein. The aP vaccine compositions of the disclosure comprise PT, FHA, and FIM2/3, and preferably PRN. These components are standard components in various marketed aP vaccines, and are available from different manufacturers (see, e.g., Table 21-3 of Chapter 21 of *Vaccines*, Plotkin 2008), and are, for instance, commercially available from List Biological Laboratories, Inc. (Campbell, Calif.). The compositions of the disclosure comprise detoxified *pertussis* toxin, also known as *pertussis* toxoid (PT). PT can be chemically or genetically detoxified. Chemical detoxification can, for instance, be performed by any of a variety of conventional chemical detoxification methods, such as treatment with formaldehyde, hydrogen peroxide, tetranitromethane, or glutaraldehyde. For instance, detoxification can be performed as described on page 17 and example 3 of WO 96/34883, incorporated by reference herein. In certain embodiments, PT is genetically detoxified. This can be done by making mutations in the *pertussis* toxin gene to inactivate the enzymatic activity of the catalytic subunit S1 of *pertussis* toxin, and has, for instance, been described in U.S. Pat. Nos. 7,144,576, 7,666, 436, and 7,427,404. Particularly advantageous mutations to detoxify *pertussis* toxin are, for instance, provided in U.S. Pat. No. 7,427,404, incorporated by reference herein. A particularly advantageous embodiment is *pertussis* toxin wherein the amino acid residue Glu129 in the *pertussis* holotoxin amino acid sequence in the S1 subunit is substituted by Gly (E129G) and Arg9 is substituted by Lys (R9K) (U.S. Pat. No. 7,427,404; Buasri, *BMC Microbiology* 2012, 12: 61). Such genetically detoxified PT (E129G, R9K) can also be conveniently isolated from a genetically engineered strain that shows enhanced production of this PT (Buasri, 2012, supra). Advantages of using genetically detoxified mutants are that no or less use of hazardous chemicals is required for detoxification, improved preservation of the epitopes of the PT antigens and thus better immune responses thereto, and/or lower amounts of antigen can be used in the vaccine. In other embodiments, PT is chemically detoxified. Chemically or genetically detoxified PT is widely used in aP vaccines (see, e.g., Table 21-3 of Chapter 21 of *Vaccines, Plotkin* 2008). PT can, for instance, be obtained and purified as described in page 16 and example 2 of WO 96/34883, incorporated by reference herein. PT can also be obtained using methods as, e.g., described in U.S. Pat. No. 5,085,862, WO96/34623, U.S. Pat. No. 4,705,868, EP0336736, WO9115505, EP0306318, EP0322533, EP0396964, EP0275689, WO91/12020, EP0427462, WO9819702 and U.S. Pat. No. 4,784,589, each of which is incorporated by reference herein.

Chemically or genetically detoxified PT is available from various commercial sources. In certain embodiments, the amount of PT in a vaccine hereof is 2-50 µg, 5-40 µg, 10-30 µg, or 20-25 µg per human dose (typically 0.5 ml).

The compositions in certain embodiments comprise pertactin (PRN), a 69 kD outer membrane protein of *B. pertussis* (therefore sometimes also referred to as 69K antigen). PRN can, for instance, be obtained and purified as described on page 18-19 and example 2 of WO 96/34883, incorporated by reference herein. It can also, for instance, be obtained as described in EP0162639, EP0484621, U.S. Pat. No. 6,444, 211, U.S. Pat. No. 5,276,142, U.S. Pat. No. 5,101,014, EP0336736, WO96/34623, WO90/16651, and WO90/56076, all incorporated by reference herein. PRN can also be conveniently isolated from *B. pertussis* strains that have been genetically engineered to express high levels of PRN, such as described, for instance, in (Buasri, 2012, supra).

In certain embodiments, the amount of PRN in a vaccine hereof is 0.5-100 µg, 1-50 µg, 2-20 µg, 3-30 µg, 5-20 µg, or 6-10 µg per human dose (typically 0.5 ml) (see, e.g., EP 0928198).

The compositions hereof comprise filamentous hemagglutinin (FHA), a major 230-kDa adhesin of *B. pertussis* that is important for the adherence of *B. pertussis* to the host ciliary epithelial cells of the respiratory tract, and an established component of marketed multivalent aP vaccines. FHA can, for instance, be obtained and purified as described in page 17-18 and example 2 of WO 96/34883, incorporated by reference herein. FHA can also, for instance, be obtained as described in WO9013313, EP0484621, WO9634623, EP0336736, WO9115505, U.S. Pat. No. 4,784,589, and WO9004641, all incorporated by reference herein.

In certain embodiments, the amount of FHA in a vaccine hereof is 2-50 µg, 5-40 µg, 10-30 µg, or 20-25 µg per human dose (typically 0.5 ml).

The compositions hereof comprise fimbrial agglutinogens 2 and 3, also referred to as fimbriae 2 and 3 or agglutinogens 2 and 3 or Agg 2 and 3 (herein referred to as FIM2 and FIM3, or as "FIM" or "FIM2/3," which is a combination of FIM2 and FIM3 as a mix). Typically, in a composition, according to the disclosure, the weight ratio of FIM 2 to FIM 3 is from about 1:3 to about 3:1, e.g., from about 1:1 to about 3:1, e.g., from about 1.5:1 to about 2:1. Preparation of FIM is described in detail in page 12-13 and example 2 of WO 96/34883, incorporated by reference herein. FIM can also, for instance, be obtained as described in WO9634623, U.S. Pat. No. 4,784, 589, U.S. Pat. No. 6,475,754, EP0555894, WO9858668, and WO0207764, all incorporated by reference herein.

The amount of FIM in a vaccine or immunogenic composition hereof is 12-100 µg per human dose (typically 0.5 ml). In certain embodiments, this amount is 12-50 µg, or 12-30 µg per human dose (typically 0.5 ml). In preferred embodiments of the disclosure, the amount of FIM is at least 15 µg per human dose (typically 0.5 ml). In certain embodiments this amount is 15-100 µg, 15-80 µg, 15-60 µg, 15-50 µg, 15-30 µg or 15-25 µg per human dose (typically 0.5 ml). In further preferred embodiments of the disclosure, the amount of FIM is at least 20 µg per human dose (typically 0.5 ml). In certain embodiments this amount is 20-100 µg, 20-80 µg, 20-60 µg, 20-50 µg, 20-30 µg, 20-25 µg, or 25-50 µg per human dose (typically 0.5 ml).

FIM can be isolated from *B. pertussis*, or can be recombinantly produced, or is, for instance, commercially available from List Biological Laboratories, Inc. (Campbell, Calif.; on the World Wide Web at listlabs.com, product #186 in online catalog).

In certain embodiments, a vaccine composition, according to the disclosure, comprises per human dose (or per 0.5 ml bulk vaccine): 10-25 µg PT, 10-25 µg FHA, 3-8 µg PRN, and 12-50 µg FIM. In certain embodiments, a vaccine composition, according to the disclosure, comprises per human dose (or per 0.5 ml bulk vaccine): 20-25 µg PT, 20-25 µg FHA, 3-8 µg PRN, and 12-50 µg FIM. In certain embodiments, a vaccine composition, according to the disclosure, comprises per human dose (or per 0.5 ml bulk vaccine): 20-25 µg PT, 20-25 µg FHA, 3-8 µg PRN, and 12-25 µg FIM. In a certain embodiment, the disclosure provides a vaccine comprising per human dose (or per 0.5 ml bulk vaccine): about 20 µg PT, about 20 µg FHA, about 3 µg PRN, and about 15-20 µg FIM.

One simple way of preparing a vaccine hereof is to add commercially available FIM to a commercially available aP5 vaccine. A vaccine of the disclosure can also be simply prepared by adding FIM to a commercially available aP vaccine that comprises PT and FHA but not yet FIM (aP2), or a commercially available aP vaccine that comprises PT, FHA and PRN but not yet FIM (aP3). In certain embodiments, the FIM may first be adsorbed to an adjuvant if so desired, e.g., to aluminum hydroxide and/or aluminum phosphate, before adding to the other components. In other embodiments, the FIM is added to the other components without prior adsorption to adjuvant.

The term "about" for numerical values, as used herein, means the value±10%.

The compositions of the disclosure may in certain embodiments also comprise non-*pertussis* protein components, e.g., to obtain combination vaccines (Decker, M. D., Edwards, K. M. & Bogaerts, H. H. Combination vaccines. In *Vaccines* (Eds. Plotkin, S., Orenstein, W. A. & Offit, P. A.) Elsevier Health Sciences, 2008. 1069-1101). In certain embodiments, the compositions hereof may therefore further comprise antigens derived from one or more pathogens other than *B. pertussis*. In certain embodiments, the compositions hereof comprise one or more of the following: tetanus toxoid (TT), *diphtheria* toxoid (DT), *Haemophilus influenzae* type-b oligosaccharide or polysaccharide conjugate (Hib), hepatitis B virus surface antigen (HBsAg), inactivated polio virus (IPV).

Combination vaccines of aP with such non-*pertussis* components are known and widely used. Preparation of combination vaccines has, for instance, been described in WO2010/046935, U.S. Pat. No. 6,013,264, WO2007/054820, WO98/000167, and EP1946769, all incorporated by reference.

In certain embodiments, the aP5 (or aP4: PT, FHA, FIM2/3), according to the disclosure, is in a composition that further comprises DT and TT, thus providing for a DTaP5 (or DTaP4) vaccine, according to the disclosure. DTaP5 vaccines are widely used to prevent *diphtheria*, tetanus and whooping cough. The vaccine hereof has a higher amount of FIM than the DTaP5 vaccines described before, and is more efficacious against PRN-negative *B. pertussis* strains than conventional DTaP5 vaccines.

One way for isolating, purifying and detoxifying DT is described in page 33-34 of WO 96/34883, incorporated by reference herein. DT can also, for instance, be obtained as described in U.S. Pat. No. 4,709,017, U.S. Pat. No. 5,843,711, U.S. Pat. No. 5,601,827, U.S. Pat. No. 5,917,017, and WO96/34623, all incorporated by reference.

One way for isolating, purifying and detoxifying TT is described in page 34-36 of WO 96/34883, incorporated by reference herein. TT can also, for instance, be obtained as described in EP0209281, EP0478602, and WO96/34623, all incorporated by reference.

Hib oligosaccharide or polysaccharide conjugate can, for instance, be obtained as described in WO2007/054820, WO2004/110480, U.S. Pat. No. 6,333,036, WO2010/046935, U.S. Pat. No. 4,372,945, U.S. Pat. No. 4,474,757, WO95/08348, WO2010/046935, U.S. Pat. No. 4,673,574, EP0161188, EP0208375, and EP0477508, all incorporated by reference. Hib antigen can, for instance, be the capsular polysaccharide of Hib, or a conjugate of the polysaccharide or a derived oligosaccharide thereof to a carrier protein such as DT, TT, or $CRM_{197}$, a nontoxic variant of *diphtheria* toxin isolated from *Corynebacterium diphtheriae* C7 (b197).

HBsAg can, for instance, be obtained as described in EP0226846, EP0299108, U.S. Pat. No. 6,013,264, WO2007/054820, WO2010/046935, and WO9324148, all incorporated by reference.

IPV can be monovalent, containing one type of poliovirus (type 1, 2 or 3), or divalent (containing two types of poliovirus, e.g., types 1 and 2, 1 and 3 or 2 and 3), or trivalent (containing three types of poliovirus, i.e., types 1, 2 and 3). Preferably, the IPV, according to the disclosure, contains inactivated poliovirus types 1, 2 and 3. IPV can, for instance, be obtained as described in U.S. Pat. No. 4,525,349, and WO2011/006823, incorporated by reference herein.

These non-*pertussis* components can be obtained from various manufacturers. Examples are described in ("Vaccines." 5th edition. S. Plotkin, W. Orenstein, P. Offit, 2008, Section 2, Chapter 38 ("Combination vaccines," M. D. Decker, K. M. Edwards, H. H. Bogaerts, p 1069-1101)).

In certain embodiments, the compositions hereof comprise a composition comprising the *pertussis* components (aP5 or aP4 vaccine) according to any one of the embodiments described above (i.e., comprising 12-100 µg FIM per human dose and PT, FHA and optionally PRN; hereinbelow referred to as "aP, according to the disclosure," or "aP5*" for brevity), and DT.

In certain embodiments, the compositions hereof comprise aP, according to the disclosure, and TT.

In certain embodiments, the compositions hereof comprise aP, according to the disclosure, and IPV (referred to herein as "aP5*-IPV").

In certain embodiments, the compositions hereof comprise aP, according to the disclosure, DT and TT (referred to herein as "DTaP5*").

In certain embodiments, the compositions hereof comprise aP, according to the disclosure, DT, TT and Hib (referred to herein as "DTaP5*-Hib).

In certain embodiments, the compositions hereof comprise aP, according to the disclosure, DT, TT and IPV (referred to herein as "DTaP5*-IPV").

In certain embodiments, the compositions hereof comprise aP, according to the disclosure, DT, TT and HBSAg (referred to herein as "DTaP5*-HepB").

In certain embodiments, the compositions hereof comprise aP, according to the disclosure, DT, TT, Hib and HBSAg (referred to herein as "DTaP5*-Hib-HepB").

In certain embodiments, the compositions hereof comprise aP, according to the disclosure, DT, TT, Hib and IPV (referred to herein as "DTaP5*-Hib-IPV").

In certain embodiments, the compositions hereof comprise aP, according to the disclosure, DT, TT, HBSAg and IPV (referred to herein as "DTaP5*-HepB-IPV").

In certain embodiments, the compositions hereof comprise aP, according to the disclosure, DT, TT, Hib, HBSAg and IPV (referred to herein as "DTaP5*-Hib-HepB-IPV").

Further non-*pertussis* components could optionally be added, e.g., components that are sometimes combined with aP in combination vaccines, such as antigens from meningococci and/or pneumococci.

For the combination vaccines, the amounts of the non-*pertussis* components may be varied. Generally, the amounts of these components as typically present in individual or combination vaccines can be used according to the instant disclosure. See, for instance, "Vaccines." 5th edition. S. Plotkin, W. Orenstein, P. Offit, 2008, Section 2, for the various components and combination vaccines; in particular, Chapter 38 describes combination vaccines including aP vaccines with the components mentioned above (Decker, pp 1069-1101); Chapter 10 describes DT (Vitek, pp 139-156); Chapter 31 describes TT (Wassilak, pp 805-840); Chapter 25 describes IPV vaccines (Plotkin, pp 605-630); Chapter 11 describes Hib vaccines (Chandran, pp 157-176); and Chapter 13 describes Hepatitis B vaccines (based on HBsAg) (Mast, pp 205-242), all incorporated by reference. Non-limiting examples of suitable amounts (it is also common to express amounts of DT and TT in IU or in Lf (flocculation units), see, e.g., (Decker, In: *Vaccines*, pp 1069-1101, supra), but here we provide micrograms) of the antigens per dose would, for instance, be: 1-100 µg, e.g., 2-40 µg, e.g., 6-25 µg, e.g., 15-25 µg DT; 1-50 µg, e.g., 2-20 µg, e.g., 5-10 µg TT; 1-100 µg, e.g., 3 to 40 µg of HBsAg protein per milliliter; 0.1-100 µg, e.g., 0.2 to 50 µg, e.g., 1 to 25 µg, e.g., 2-10 µg of the Hib capsular polysaccharide or oligosaccharide thereof in the form of a conjugate to a carrier protein; wild type-derived IPV-containing products (wt-IPV) are generally formulated to contain 40-8-32 D-Ag units per dose for poliovirus types 1, 2 and 3, respectively. However, these amounts may also be varied, e.g., lower amounts such as 10-20 D-Ag units for IPV type 1 can also be used, and the amounts for IPV types 2 and 3 can also be varied (see, e.g., EP 2066344). Amounts may also vary according to the intended use, e.g., booster vaccines may in certain embodiments contain less units of certain components than priming vaccines.

The protein components in the compositions are intended to induce an immune response upon administration to an eligible subject. It will be clear to the skilled person that wherever is referred herein to proteins or mutants thereof, e.g., toxoids, parts of the proteins may also be used and can have equivalent or in some cases preferred properties for inducing immune responses. Further, the proteins may contain (additional) mutations, such as deletions, insertions, substitutions, etc. Thus, immunogenic fragments and variants of the indicated protein components are included within the meaning of the proteins indicated herein.

Compositions hereof can be used as acellular *pertussis* vaccines, or as components of combination vaccines, which generate immune responses to one or more of the components in the compositions upon administration to eligible subjects. The immune response may comprise a cellular and/or a humoral response. Such immune responses preferably confer protection against infection with pathogen or against disease or at least reduces the severity of the symptoms caused by the pathogen from which the respective components are derived (i.e., in any case preferably against *B. pertussis*, and preferably also against PRN-negative mutants thereof). The compositions hereof can thus suitably be referred to as vaccines. A dose of a vaccine is the amount that is administered in a single administration to a subject. A subject may suitably be an animal or a human, and in certain embodiments the subject is a human. Many vaccines are suitably, and actually preferably, administered more than one time to the same individual with sufficient time interval to obtain a boosting effect in the individual, e.g., at least four weeks, to several years up to about two decades between administrations. Multiple immunizations are usually administered to naive infants. The compositions hereof may also be administered more than one time, e.g., in a non-limiting embodiment two or three or more times with at least 4 weeks interval, for instance, a one or two month time interval between each administration. One non-limiting example is administration according to the EPI schedule, at 6 weeks, 10 weeks and 14 weeks of age. Another regimen would be at 2 months, 4 months, 6 months of age. In certain embodiments a booster vaccination is given 10-20 years later, e.g., during adolescence. Further decennial booster vaccinations may be given. In certain embodiments, aP, according to the disclosure, is administered two or three times in the first year of life, a further boost is administered the second year of life, and a further booster is administered at four to five years of age, after which an adolescent boost is administered at approximately twelve years of age. Also the Td (a TT-DT containing vaccine given to adolescents) booster recommendation may be followed, i.e., every ten years and replace Td with Tdap, wherein the acellular *pertussis* component is aP, according to the disclosure. However, it will be clear to the skilled person that the vaccination scheme of the aP vaccines hereof may be suitably varied, as is clear from the wide variety of immunization schedules (regimens) of marketed aP vaccines by different national authorities (e.g., Table 21-5 in "Vaccines." 5$^{th}$ edition. S. Plotkin, W. Orenstein, P. Offit, 2008, Section 2, Chapter 21 *"Pertussis* vaccines," K. M. Edwards & M. D. Decker. p. 467-517).

The compositions hereof may also be suitably used as booster vaccines for populations that have been previously vaccinated by other vaccines, be those wP or aP vaccines of different composition or combination vaccines comprising wP or aP of different composition than the vaccines of the disclosure. Such boosters may, for instance, be used for vaccination of adults or elderly that have not been vaccinated against *B. pertussis* for more than a decade. It could be useful to repeat such booster vaccinations, e.g., about once every five, ten or fifteen years. It has also been recommended to administer tetanus toxoid, reduced *diphtheria* toxoid and acellular *pertussis* vaccine (Tdap) to pregnant women with every pregnancy irrespective of previous Tdap history. In certain embodiments, the aP, according to the disclosure, is administered to an infant, a child, an adolescent, an adult, an elderly, or a pregnant woman, e.g., as aP or as Tdap.

The compositions hereof are preferably pharmaceutical compositions. Such compositions comprise a composition, according to the disclosure, and typically a pharmaceutically acceptable carrier or excipient. In the present context, the term "pharmaceutically acceptable" means that the carrier or excipient, at the dosages and concentrations employed, will not cause unwanted or harmful effects in the subjects to which they are administered. Such pharmaceutically acceptable carriers and excipients are well known in the art (Remington. The Science and Practise of Pharmacy, Mack Publishing Company 1990; Frokjaer, S. & Hovgaard, L. Pharmaceutical Formulation Development of Peptides and Proteins, 2000; Handbook of Pharmaceutical Excipients, Pharmaceutical Press 2000). The compositions preferably are formulated and administered as a sterile solution. Sterile solutions are prepared by sterile filtration or by other methods known per se in the art. The solutions can then be lyophilized or filled into pharmaceutical dosage containers. The pH of the solution generally is in the range of pH 3.0 to 9.5, e.g., pH 5.0 to 7.5. The components of the composition typically are in a solution having a suitable pharmaceutically acceptable buffer, and the solution may also contain a salt. In certain embodiments, detergent is present. In certain embodiments, the vaccine may be formulated into an injectable preparation. These formulations contain effective amounts of the protein components, are either sterile liquid solutions, liquid suspensions or lyophilized versions and optionally contain stabilizers or excipients. Several examples of suitable formulations for the storage and for pharmaceutical administration of aP vaccines or combination vaccines are known (e.g., Tables 21-3 and 21-4 in ("Vaccines." 5th edition. S. Plotkin, et al, supra)). Examples of suitable diluents are PBS or saline. Preservative may optionally be present, e.g., phenoxyethanol, thimerosal or parabens. If a preservative is present, it is preferably present at low levels. In case a combination vaccine comprises IPV, the use of thimerosal is preferably avoided, since thimerosal may lead to loss of potency of the IPV component (see, e.g., Sawyer L A, 1994, Vaccine 12: 851-856; EP 2066344). Further components that may optionally be present as trace constituents are polysorbate-80, gelatin and remnants from chemical toxoidation (e.g., if PT is chemically toxoided) such as glutaraldehyde, formaldehyde.

Preferably, the vaccines hereof are stored between 2-8° C.

In certain embodiments, the compositions hereof comprise one or more adjuvants. Adjuvants are known in the art to further increase the immune response to an applied antigenic determinant (for a review on adjuvants, see, e.g., Montomoli, 2011, Expert Rev Vaccines 10: 1053-1061). Examples of suitable adjuvants include aluminum salts such as aluminum hydroxide and/or aluminum phosphate; oil-emulsion compositions (or oil-in-water compositions), including squalene-water emulsions, such as MF59 (see, e.g., WO 90/14837); saponin formulations, such as, for example, QS21 and Immunostimulating Complexes (ISCOMS) (see, e.g., U.S. Pat. No. 5,057,540; WO 90/03184, WO 96/11711, WO 2004/004762, WO 2005/002620); Toll-like receptor (TLR) agonists, e.g., a TLR7 agonist (see, e.g., WO 2012/117377, page 15-18, for examples), e.g., in combination with an aluminum salt, e.g., aluminum hydroxide to which the TLR agonist may be adsorbed; bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like. For example, PT and tetanus toxoid also have adjuvant properties of their own. In certain embodiments, the compositions of the disclosure comprise aluminum as an adjuvant, e.g., in the form of aluminum hydroxide, aluminum phosphate, aluminum potassium phosphate, or combinations thereof, in concentrations of 0.05-5 mg, e.g., from 0.075-1.0 mg, of aluminum content per dose.

In other embodiments, the compositions used do not comprise further adjuvants.

Preferably, the vaccine compositions hereof comprise an adjuvant. In certain embodiments, the adjuvant is an aluminum salt such as aluminum phosphate, aluminum hydroxide or a combination thereof. Preferably, one, more or all of the aP antigens are adsorbed onto an aluminum salt. Also, the other antigens may be adsorbed onto an aluminum salt. In certain embodiments, one, more or all of the aP antigens (PT, FHA, FIM, PRN, if present) are adsorbed onto aluminum hydroxide. In certain embodiments, one, more or all of the aP antigens (PT, FHA, FIM, PRN, if present) are adsorbed onto aluminum phosphate. Formulation of aP vaccines and aP combination vaccines with aluminum salts is, for instance, described in (Denoël, 2002, Vaccine 20: 2551-2555). Typically, the individual components are individually adsorbed onto the aluminum salt, and the components are thereafter mixed to form the vaccine formulation. This also allows to prepare vaccines in which certain components are adsorbed onto a first aluminum salt (e.g., $Al(PO_4)$), while other components are adsorbed onto a second aluminum salt (e.g., $Al(OH)_3$). Also, the other components of a combination vaccine may be adsorbed onto an aluminum salt, e.g., DT and TT may be adsorbed onto aluminum hydroxide or aluminum phosphate, or a combination of these. The DT and TT components may be adsorbed to the same or to a different aluminum salt as the aP components. Further components of combination vaccines of increasing valency may also be adsorbed onto aluminum salts, e.g., HBsAg, Hib and/or IPV may or may not be adsorbed onto aluminum salts. In certain embodiments wherein a combination vaccine comprises HBsAg, the HBsAg is adsorbed onto aluminum phosphate (see, e.g., WO 93/24148). If Hib is included in the combination vaccine and certain other components such as one or more of DT, TT or aP are adsorbed onto aluminum hydroxide, the risk of interference (reduction of efficacy of the Hib component) can be reduced, for instance, by adsorbing Hib onto aluminum phosphate or use Hib that is not adsorbed onto an aluminum adjuvant, and combine this with the other components by either contemporaneously (i.e., just prior to administration) adding the Hib, or by mixing with the other components that have been adsorbed onto aluminum hydroxide adjuvant in such a manner that the aluminum hydroxide adjuvant has been pre-saturated, as described in detail in WO 99/48525. The skilled person, thus, is aware of various ways of formulating combination vaccines hereof in a suitable manner.

In certain embodiments, a vaccine composition comprises PT, FHA, FIM2/3, and aluminum hydroxide, and optionally PRN. In certain embodiments, a vaccine composition, according to the disclosure, comprises PT, FHA, FIM2/3, and aluminum phosphate, and optionally PRN. In certain embodiments, a vaccine composition, according to the disclosure, comprises PT, FHA, FIM2/3, aluminum hydroxide and aluminum phosphate, and optionally PRN. In certain embodiments, a vaccine composition, according to the disclosure, comprises DTaP5*, and aluminum hydroxide. In certain embodiments, a vaccine composition, according to the disclosure, and aluminum phosphate. In certain embodiments, a vaccine composition, according to the disclosure, comprises DTaP5*, aluminum hydroxide and aluminum phosphate. In certain embodiments, a vaccine composition, according to the disclosure, comprises aP5*-IPV, and aluminum hydroxide or aluminum phosphate or aluminum hydroxide and aluminum phosphate. In certain embodiments, a vaccine composition, according to the disclosure, comprises DTaP5*-IPV, and aluminum hydroxide or aluminum phosphate or aluminum hydroxide and aluminum phosphate. In certain embodiments, a vaccine composition, according to the disclosure, comprises DTaP5*-Hib, and aluminum hydroxide or aluminum phosphate or aluminum hydroxide and aluminum phosphate. In certain embodiments, a vaccine composition, according to the disclosure, comprises DTaP5*-HepB, and aluminum hydroxide or aluminum phosphate or aluminum hydroxide and aluminum phosphate. In certain embodiments, a vaccine composition, according to the disclosure, comprises DTaP5*-Hib-HepB, and aluminum hydroxide or aluminum phosphate or aluminum hydroxide and aluminum phosphate. In certain embodiments, a vaccine composition comprises DTaP5*-Hib-IPV, and aluminum hydroxide or aluminum phosphate or aluminum hydroxide and aluminum phosphate. In certain embodiments, a vaccine composition comprises DTaP5*-HepB-IPV, and aluminum hydroxide or aluminum phosphate or aluminum hydroxide and aluminum phosphate. In certain embodiments, a vaccine composition, according to the disclosure, comprises DTaP5*-Hib-HepB-IPV, and aluminum hydroxide or aluminum phosphate or aluminum hydroxide and aluminum phosphate.

Administration of the compositions hereof can be performed using standard routes of administration. Non-limiting embodiments include parenteral administration, such as by injection, e.g., intradermal, intramuscular, transcutaneous, intranasal, etc. In one embodiment the vaccine is administered by intramuscular injection into the thigh or into the deltoid muscle. The skilled person knows the various possibilities to administer a vaccine hereof in order to induce an immune response to at least one of the antigens in the vaccine. Generally, the standard dose of *pertussis* vaccine is 0.5 mL given intramuscularly in the anterolateral thigh or, if necessary, the deltoid. However, the amount of the components in the compositions provided to a patient during one administration can be varied as is known to the skilled practitioner. Also the adjuvant, if used, can be adapted to the delivery system.

Although it is preferred to have a single composition for vaccinating against *pertussis*, the skilled person will be aware that the effect of the disclosure, as described herein, can also be obtained by vaccinating with the components of the aP vaccine, i.e., PT, FHA, FIM at a human dose of 12-100 µg, and optionally PRN, wherein the components are not necessarily all in the same composition, e.g., wherein (part of) the FIM is in a separate composition. For instance, a commercially available aP vaccine (having FIM at a dose of 0-5 µg per human dose) could be complemented by co-administration of FIM as a separate component to a total dose administered of 12-100 µg, e.g., 15-80 µg, 20-60 µg, 20-50 µg, or 20-25 µg FIM, e.g., by injecting a first aP vaccine composition comprising PT, FHA, optionally a dose of 5 µg FIM, and optionally PRN and injecting a separate composition comprising the (remainder of the) FIM to supplement to a total dosage of 12-100 µg, e.g., 15-80 µg, 20-60 µg, 20-50 µg or 20-25 µg FIM. In such embodiments, co-administration means that the separate compositions are administered (e.g., injected) within one hour, preferably within a few minutes between the administrations, preferably they are administered essentially simultaneously (e.g., by co-injection or by consecutive injections). Alternatively, compounds might be mixed just prior to administration, so that a single injection (with a composition that is a composition, according to the disclosure) is sufficient. The disclosure, hence, also provides a method for vaccinating a human subject against *Bordetella pertussis*, optionally a PRN-negative strain of *Bordetella pertussis*, comprising administering to the subject the following *Bordetella pertussis* antigens: *pertussis* toxoid (PT), filamentous hemagglutinin (FHA), and fimbriae types 2 and 3 (FIM), and optionally pertactin (PRN), wherein FIM is administered in an amount of 12-100 µg. In preferred embodiments, this is done by administering a single composition, according to the disclosure.

The disclosure is further described by the following illustrative Examples. The examples do not limit the disclosure in any way; they merely serve to clarify the disclosure.

EXAMPLES

Example 1

High Dose FIM in aP5 Vaccine Improves Protection Against PRN-Negative *B. pertussis*

Methods:

A validated mouse *Bordetella pertussis* lung challenge model, which correlates with clinical efficacy of aP vaccines, (Guiso, 1999, *Vaccine* 17; 2366-2376; Denoel, 2005, *Vaccine* 23:5333-5341; Godfroid, 2004, *Int. J. Med. Microbiol.* 294; 269-276) was used to test the efficacy of a licensed 5-component acellular *pertussis* vaccine (ADACEL™, Sanofi Pasteur; in this example further referred to as aP5) at a quarter of a human dose with or without the addition of 2 μg of purified FIM2/3 antigen (List Biological Laboratories Inc.). Each 0.5 mL dose of ADACEL™ contains 5 Lf tetanus toxoid, 2 Lf *diphtheria* toxoid and 5 acellular *pertussis* antigens (2.5 μg detoxified *pertussis* toxin, 5 μg filamentous hemagglutinin, 3 μg pertactin and 5 μg fimbriae types 2 and 3). In brief, female Balb/c mice were vaccinated subcutaneously with aP5 with or without FIM2/3 antigen at 4 and 7 weeks of age at ¼ of the human dose. Therefore, animals received either 1.25 μg of FIM2/3 (aP5 group) or 3.25 μg of FIM2/3 (aP5+FIM group), which equals 5 μg and 13 μg in humans, respectively. At 9 weeks of age, the mice were challenged intranasally with ~$10^6$ cfu of *B. pertussis* WHO 18323 (a pertactin positive strain), a pertactin-negative strain PRN-STOP and a pertactin-negative strain PRN-IS (Queenan, 2013, *N Engl J Med.* 368: 583-4). At 2 hours, 2 days, 5 days and 8 days post-challenge (n=5/group) lung clearance was determined by counting the *B. pertussis* colonies grown on Bordet-Gengou agar plates after plating serial dilutions of lung homogenate.

Results:

The treatment response-over time profile after vaccination with aP5 with or without the addition of FIM2/3 antigen is depicted in FIG. 1. To test for a statistically significant difference between mean log 10 CFU counts on day 5 and day 8 between mice vaccinated with aP5 or aP5+FIM, the Wilcoxon Exact Test was used. In addition, the treatment response over time (from day 0 to day 8) profile data was modeled by an analysis of covariance (Milliken G A et al. Analysis of Covariance, Dept. of Statistics, Kansas State University, 1989.; SAS Institute Inc., SAS/STAT User's Guide, Version 6, Fourth Edition, Volume 2. Cary, N.C.: SAS Institute Inc., 1989).

For the *B. pertussis* WHO18323 strain (a PRN positive strain, FIG. 1A), a comparison of difference in log 10 CFU counts at day 5 using a one-sided Wilcoxon's exact nonparametric test, showed that mean log 10 CFU counts after vaccination with aP5+FIM were significantly lower ($p<0.05$) than those after vaccination with aP5 alone. Modelling of sample treatment response-time profile data showed no statistically significant difference in treatment response from day 0 to day 8 from a fitting by an analysis of covariance with day as a term for slope and day*day as a term for quadratic curvature.

After challenge with the *B. pertussis* PRN-STOP strain (FIG. 1B), a comparison of difference in log 10 CFU counts at day 5 using a one-sided Wilcoxon's exact nonparametric test showed that mean log 10 CFU counts after vaccination with aP5+FIM were significantly lower ($p<0.02$) than those after vaccination with aP5 alone. Modeling of sample treatment response-time profile data showed no statistically significant difference in treatment response from day 0 to day 8 from a fitting by an analysis of covariance model.

For the *B. pertussis* PRN-IS strain (FIG. 1C), a comparison of difference in log 10 CFU counts at day 5 indicated no significant differences between vaccine treatments using a one-sided Wilcoxon's exact nonparametric test. On day 8 there was a trend that mean log 10 CFU counts were lower after vaccination with aP5+FIM compared with mean log 10 CFU counts after vaccination with aP5 alone ($P<0.08$) using Wilcoxon's exact nonparametric test. The asymptotic analog of the Wilcoxon's exact test showed a significant vaccine difference on day 8 ($p<0.03$). Modeling of sample treatment response-time profile data suggested a difference in treatment response from day 0 to day 8 from fitting by an analysis of covariance with day as a term for slope and day*day*trt as a term quadratic curvature.

To test for a difference in treatment effects, a linear contrast between treatment profiles from day 0 to day 8 indicated that mean log 10 CFU counts after vaccination with aP5+FIM were significantly lower ($p<0.01$) than those measured after vaccination with aP5 alone.

In summary, these results show that addition of 2 μg of FIM2/3 to $1/4^{th}$ of a human dose of ADACEL™ vaccine significantly increases the efficacy of this vaccine in a mouse nasopharyngeal challenge model against a PRN-negative *B. pertussis* isolate. This finding is surprising since there have not been any previous suggestions that increasing the amount of FIM in a *pertussis* vaccine would increase its efficacy. This result is specifically relevant in the context of PRN-negative strains that are currently emerging and causing disease around the world.

Example 2

Increased Vaccine Efficacy after Addition of FIM in the Mouse Challenge Model is Dose Dependent Methods:

To investigate whether an increased dose of FIM correlated with increased vaccine efficacy, which would suggest the effect to be FIM-specific, the validated mouse *Bordetella pertussis* lung challenge model as described above was used. Animals were vaccinated with a 1/10 human dose of a licensed 2-component aP vaccine (PENTAVAC®, Sanofi Pasteur MSD; vaccine hereinafter referred to as aP2) with or without the addition of FIM2/3 (List Biological Laboratories Inc.; material further referred to as FIM). Each human 0.5 mL dose of PENTAVAC® contains: (at least) 40 IU tetanus toxoid (TT); (at least) 30 IU *diphtheria* toxoid (DT); 40, 8 and 32 D-antigen units of inactivated poliovirus (IPV) types 1, 2 and 3 respectively; 10 μg *H. Influenzae* type B polysaccharide conjugated to TT (Hib-TT); and 2 acellular *pertussis* antigens (25 μg detoxified *pertussis* toxin (PT) and 25 μg filamentous hemagglutinin (FHA)). An amount of 0.5; 1.0; 1.5; 2.0; 2.5 or 5.0 μg FIM, corresponding to 5, 10, 15, 20, 25 or 50 μg FIM per human dose, respectively, was adsorbed to aluminum hydroxide and co-administered (as a separate injection) with the licensed aP2 vaccine (thus mimicking an aP vaccine with high dose of FIM, according to the disclosure). At 9 weeks of age, the mice were challenged intranasally with ~$10^6$ cfu of a PRN-negative *B. pertussis* strain (I195). At 2 hours (n=5/group) and 5 days (n=10/group) lung clearance was determined by counting the *B. pertussis* colonies grown on Bordet-Gengou agar plates after plating serial dilutions of lung homogenate.

Results:

A dose-dependent decrease in the number of *B. pertussis* colonies cultured from the lungs of vaccinated mice was observed with an increasing amount of FIM. Similarly, a dose-dependent decrease in the number of *B. pertussis* colonies cultured from the lungs of vaccinated mice was observed in mice vaccinated with a 1/25 dilution and increasing amounts of FIM. FIG. 2 shows the log 10 CFU counts obtained from the lungs of mice vaccinated with 1/10 human dose of aP2 in the presence of an increasing amount of FIM, 5 days post challenge with *B. pertussis* strain I195. Table 1 shows mean Log 10 CFU counts and p-values calculated using Mann-Whitney (GraphPad Prism) comparing mean log 10 CFU counts after vaccination with aP2 at 1/10 human dose with or without FIM. After the addition of 2 μg or more of FIM to aP2 1/10 human dose (human dose equivalent of 20 μg), vaccine efficacy increased significantly.

Conclusions:

The dose dependent effect of an increased FIM dose on vaccine efficacy demonstrates this effect is specific for FIM. In addition, vaccines including a high dose of FIM are more efficacious than a vaccine containing the maximum amount of FIM present in currently commercially available aP5 vaccines (5 μg per human dose). This is in line with the findings in example 1 that showed that increasing the dose of FIM in aP vaccine above 10 μg per human dose improved the efficacy, and further extends the findings to a different aP vaccine and an additional PRN-negative *pertussis* strain.

Example 3

Increased Efficacy of an aP5 Vaccine with the Addition of FIM is Observed Against Multiple *B. pertussis* Strains Methods:

The validated mouse *Bordetella pertussis* lung challenge model as described above was used to investigate whether an increased dose of FIM improved vaccine efficacy against a variety of *B. pertussis* strains. A 1/10 human dose of ADACEL® (Sanofi Pasteur; containing 2.5 μg PT, 5 μg FHA, 3 μg PRN and 5 μg FIM2/3 per human dose, see also example 1; herein referred to as aP5) or BOOSTRIX® (GlaxoSmith-Kline Biologicals; containing 5 Lf of tetanus toxoid, 2.5 Lf of *diphtheria* toxoid, 8 μg PT, 8 μg FHA and 2.5 μg PRN per human dose; herein referred to as aP3) was used, with or without the addition (as separate injection after adsorption to aluminum hydroxide) of 5 μg of FIM (List Biological Laboratories Inc.), corresponding to 50 μg per human dose. Animals that were vaccinated at 4 and 7 weeks of age, were challenged at 9 weeks of age with one of the following *B. pertussis* strains: WHO 18323 (PRN-positive), 24422 (PRN-negative), 24421 (PRN-negative) or I195 (PRN-negative). At 2 hours (n=5/group) and 5 days (n=10/group) lung clearance was determined by counting the *B. pertussis* colonies grown on Bordet-Gengou agar plates after plating serial dilutions of lung homogenate.

Results:

Addition of 5 μg of FIM to a 1/10 human dose of aP5 improved vaccine efficacy against all *B. pertussis* strains, which reached statistical significance against 3 of the tested *pertussis* strains (WHO 18323 (p=0.04), PRN-24421 (p=0.03) and PRN-I195 (p=0.001)) (FIG. 3, Table 2).

This experiment was also performed using aP3 (1/10 human dose). For three of the challenge strains (WHO 18323, 24422 and 24421) a reduction after addition of FIM was not observed with this aP3 vaccine (BOOSTRIX®), although this might possibly partly be explained by the already high efficacy observed for these challenge strains with this particular aP3 when given without FIM. A significant reduction in log 10 CFU counts was however observed with the addition of FIM to this aP3 when challenging with *B. pertussis* strain I195.

Overall, these data indicate that a vaccine with a high dose of FIM would have an improved efficacy against a range of *pertussis* strains.

Conclusions:

The increased efficacy observed after immunization with a high level of FIM in combination with a commercially available aP5 vaccine against a panel of *B. pertussis* strains indicates the benefit of a high FIM dose is observed also against different *pertussis* strains. Therefore, vaccines including a high dose of FIM, according to the disclosure, could contribute to decreasing the rate of *pertussis* disease.

Example 4

Increased Efficacy with the Addition of FIM for Different Currently Commercially Available aP Vaccines Methods:

The validated mouse *Bordetella pertussis* lung challenge model as described above was used to investigate whether an increased dose of FIM (List Biological Laboratories Inc.) improved vaccine efficacy of ADACEL® (Sanofi Pasteur; containing 2.5 μg PT, 5 μg FHA, 3 μg PRN and 5 μg FIM 2+3 as aP components per human dose), PENTAVAC® (Sanofi Pasteur MSD; containing 25 μg PT and 25 μg FHA as aP components per human dose) or BOOSTRIX® (GlaxoSmith-Kline Biologicals; containing 8 μg PT, 8 μg FHA and 2.5 μg PRN as aP components per human dose).

Mice were vaccinated with 1/10 human dose at 4 and 7 weeks of age with or without the addition of 5 μg FIM to the commercial vaccine (corresponding to 50 μg FIM added per human dose), challenged at 9 weeks of age with *B. pertussis* pertactin-negative strain I195 and lung clearance was determined 5 days post-challenge (n=10/group) by counting the *B. pertussis* colonies grown on Bordet-Gengou agar plates.

Results:

For all three vaccines the addition of FIM resulted in significantly lower mean Log 10 CFU counts compared to mean Log 10 CFU counts after vaccination with the commercial vaccine alone (Table 3).

Conclusion:

The vaccine efficacy of all three vaccines improved significantly after the addition of FIM. This suggests the effect of FIM can be generalized to a range of commercial aP vaccines that contain different amounts of *pertussis* antigens and different amounts of FIM. Efficacy of vaccines that already include FIM (ADACEL®) or those that do not include FIM (PENTAVAC® or BOOSTRIX®) improves, showing that it is not just presence of FIM that contributes to vaccine efficacy, but that also the dose of FIM is important.

Example 5

Increased Anti-FIM Antibody Functionality after Vaccination with a High Dose of FIM Against a Wide Range of *Pertussis* Strains Functional activity of antibodies against *pertussis* components have been identified as important additional parameters to consider, in particular when evaluating new formulations containing PT and FIM, which are known to induce antibodies with functional activity such as toxin neutralization and bacterial agglutination, respectively. Assays to measure whole-cell *B. pertussis* agglutinating antibodies have been established. Although there is no functional threshold that has been found to correlate directly with the protective efficacy of *pertussis* vaccines, they are nevertheless an important immune parameter to determine as part of the overall comparison of new vaccine formulations to those proven to be safe and effective (from WHO draft Recommendations for aP vaccines, WHO/BS/2011.2158, section C.2.1.2). Thus, given the relevance of such assays for FIM containing aP vaccines, we used an agglutination assay to further test the vaccines of the disclosure against various *B. pertussis* strains.

Methods:

Serum was collected from mice that were vaccinated at 4 and 7 weeks of age with a 1/10 human dose of PENTAVAC® (Sanofi Pasteur MSD; containing as aP antigens 25 µg PT and 25 µg FHA per human dose; referred to herein as aP2) with or without the addition of FIM (List Biological Laboratories Inc.). An amount of 0.5 or 2.0 µg FIM, corresponding to 5 or 20 µg FIM per human dose, respectively, was adsorbed to aluminum hydroxide and co-administered (as a separate injection) with the commercially available aP2 vaccine. At week 9, 5 animals per dosing group were sacrificed and sera isolated from terminal bleeds were pooled for investigation of anti-FIM (functional) antibody levels. To evaluate functional antibody responses to FIM, an agglutination assay was performed. In this assay, the presence of functional antibodies in test serum leads to the formation of antigen/antibody complexes when mixed with *B. pertussis*. Positive agglutination is defined as the presence of an opaque solution in the well, due to the presence of antigen/antibody complexes. Negative agglutination is observed as a defined bacterial sediment at the bottom of the well. In brief, 50 µl of test serum was serially diluted in PBS and mixed with 50 µl of a *B. pertussis* suspension of an $OD_{600}$ of 1.0. This mixture was incubated overnight and the next day the presence or absence of a bacterial sediment was determined using an inverted mirror. The agglutination titer is defined as the highest dilution which results in complete agglutination.

To investigate whether anti-FIM antibodies induced by vaccination of mice were functional against a panel of *B. pertussis* strains it was tested whether the sera had the capacity to agglutinate to 10 different FIM expressing *B. pertussis* strains. From a panel of 30 recent clinical *B. pertussis* isolates (kindly provided by Dr. Alan Evangelista, St. Christopher's Hospital for Children in Philadelphia), 24 isolates showed clear agglutination readouts with a positive control commercial anti-FIM monoclonal antibody (06/128, NIBSC, UK), confirming these strains express the FIM antigen. From this panel of 24 strains, 5 PRN-negative and 5 PRN-positive strains were selected for testing the mouse serum.

Results:

Vaccination in the presence of FIM induced functional antibody titers. Positive agglutination was observed with all the 6 mouse serum pools of mice vaccinated in the presence of FIM against all 10 *B. pertussis* strains. The unvaccinated control group and the group receiving aP2 at 1/10 human dose alone, which does not include FIM, did not show any agglutination (Table 4). Although a high dose of FIM was shown to be more efficacious than a low dose of FIM in validated mouse *Bordetella pertussis* lung challenge model (example 2), there was no clear FIM dose-response correlation (data not shown for other FIM doses), which is likely due to the limitation of this WHO standardized assay, which is not sensitive enough to detect small differences in agglutination.

Conclusion:

Vaccination with a commercial vaccine in the presence of FIM results in induction of functional antibodies against a wide panel of *B. pertussis* strains, either PRN-negative or PRN-positive strains. This finding indicates that a vaccine including a high dose of FIM would be effective in reducing *pertussis* disease caused by a wide range of *B. pertussis* strains.

TABLE 1

Effect on protection of adding increasing doses of FIM to aP2 vaccine.

| | Total amount FIM | FIM equivalent Human Dose | Mean Log 10 CFU | P-value vs aP2 alone |
|---|---|---|---|---|
| Control | — | — | 7.2 | 0.0002 |
| aP2 | — | — | 2.9 | — |
| aP2 + 0.5 µg FIM | 0.5 µg | 5 µg | 3.5 | 0.3418 |
| aP2 + 1.0 µg FIM | 1.0 µg | 10 µg | 2.1 | 0.0514 |
| aP2 + 1.5 µg FIM | 1.5 µg | 15 µg | 2.5 | 0.5390 |
| aP2 + 2.0 µg FIM | 2.0 µg | 20 µg | 2.0 | 0.0164 |
| aP2 + 2.5 µg FIM | 2.5 µg | 25 µg | 1.6 | 0.0013 |
| aP2 + 5.0 µg FIM | 5.0 µg | 50 µg | 1.4 | 0.0001 |

Table 1: P-values as determined using Mann-Whitney, comparing the difference in mean Log 10 CFU counts from the lung in mice challenged with PRN-negative *B. Pertussis* strain I195 at week 9 after vaccination with aP2 at 1/10 human dose with the addition of FIM versus aP2 alone given in a 1/10 human dose at 4 and 7 weeks of age. For details see example 2.

TABLE 2

Effect of adding FIM to aP5 vaccine to protection against different strains.

| | aP5 | | | aP5 + FIM | | | |
|---|---|---|---|---|---|---|---|
| strain | Total amount FIM (μg) | FIM equivalent Human Dose (μg) | Mean Log 10 CFU | Total amount FIM (μg) | FIM equivalent Human Dose (μg) | Mean Log 10 CFU | P-value |
| WHO 18323 | 0.5 | 5 | 4.0 | 5.5 | 55 | 3.3 | 0.04 |
| 24422 | 0.5 | 5 | 4.6 | 5.5 | 55 | 3.6 | 0.08 |
| 24421 | 0.5 | 5 | 4.5 | 5.5 | 55 | 3.8 | 0.03 |
| I195 | 0.5 | 5 | 5.3 | 5.5 | 55 | 4.0 | 0.001 |

Table 2: Mean Log 10 CFU counts from the lung in mice 5 days post challenge with 4 different *B. pertussis* strains at week 9 after vaccination with aP5 at 1/10 human dose with or without the addition of 5 μg of FIM at 4 and 7 weeks of age. P-values determined using Mann-Whitney. For details see example 3.

TABLE 3

Effect of addition of FIM to different commercial aP vaccines.

| | Total amount of FIM (μg) | FIM Equivalent Human Dose (μg) | Mean Log10 CFU | P-value |
|---|---|---|---|---|
| ADACEL ® | 0.5 | 5 | 5.3 | |
| ADACEL ® + FIM | 5.5 | 55 | 3.94 | 0.001 |
| PENTAVAC ® | 0 | 0 | 2.89 | |
| PENTAVAC ® + FIM | 5 | 50 | 1.38 | 0.0001 |
| BOOSTRIX ® | 0 | 0 | 4.1 | |
| BOOSTRIX ® + FIM | 5 | 50 | 2.87 | 0.004 |

Table 3: Mean Log 10 CFU counts from the lung in mice, 5 days post challenge with *B. pertussis* strain I195 at week 9 after vaccination with 3 different licensed aP vaccines at 1/10 human dose with or without the addition of 5 μg of FIM at 4 and 7 weeks of age. P-values determined using Mann-Whitney. For details see Example 4.

TABLE 4

Functional activity of antibodies against various strains by addition of FIM to aP2 vaccine.

| | Total amount FIM (μg) | FIM equivalent Human Dose (μg) | FIM Antibody level | Agglutionation against PRN- Negative Strains | | | | Agglutionation against PRN-Positive Strains | | | | | |
|---|---|---|---|---|---|---|---|---|---|---|---|---|---|
| | | | | 1 | 2 | 3 | 4 | 5 | 6 | 7 | 8 | 9 | 10 |
| Control | — | — | < | < | < | < | < | < | < | < | < | < | < |
| aP2 | — | — | < | < | < | < | < | < | < | < | < | < | < |
| aP2 + 0.5 μg FIM | 0.5 | 5.0 | 193 | 480 | 480 | 480 | 480 | 320 | 320 | 200 | 480 | 320 | 320 |
| aP2 + 2.0 μg FIM | 2.0 | 20 | 285 | 960 | 960 | 960 | 960 | 960 | 960 | 640 | 960 | 640 | 800 |

Table 4: Anti-FIM antibody levels and agglutination titers against a panel of *B. pertussis* strains as determined in serum pools collected from 5 mice per group, vaccinated at 4 and 7 weeks of age with a 1/10 human dose of aP2 with or without the addition of FIM. See example 5 for details <: below lower limit of detection (LLOD)

What is claimed is:

1. An acellular *pertussis* (aP) immunogenic composition comprising:
    a first component comprising *Bordetella pertussis* pertussis toxoid (PT),
    a second component comprising filamentous hemagglutinin (FHA), and
    a third component consisting of fimbriae types 2 and 3 (FIM), wherein FIM is present in the composition in an amount of 12-100 μg per human dose.

2. The aP immunogenic composition of claim 1, wherein FIM is present in an amount of 15-60 μg per human dose.

3. The aP immunogenic composition of claim 2, wherein FIM is present in an amount of 20-60 μg per human dose.

4. The aP immunogenic composition of claim 3, wherein FIM is present in an amount of 20-50 μg per human dose.

5. The aP immunogenic composition of claim 4, wherein FIM is present in an amount of 20-25 μg per human dose.

6. The aP immunogenic composition of claim 1, further comprising pertactin (PRN).

7. The aP immunogenic composition of claim 1, wherein the PT is genetically detoxified.

8. The aP immunogenic composition of claim 1, further comprising:
    antigen from one or more pathogens other than *B. pertussis*.

9. The aP immunogenic composition of claim 8, wherein the antigen comprises antigens from tetanus toxoid and diphtheria toxoid.

10. The aP immunogenic composition of claim 8, further comprising one or more of:
    *Haemophilus influenzae* (Hib) oligosaccharide or polysaccharide conjugate,
    hepatitis B virus surface antigen (HBsAg), and
    inactivated polio virus (IPV).

11. The aP immunogenic composition of claim 1, further comprising an adjuvant.

12. The aP immunogenic composition of claim 11, wherein the adjuvant comprises aluminum hydroxide, aluminum phosphate, or a combination thereof.

13. A method of vaccinating a subject against *Bordetella pertussis*, the method comprising:
   administering to the subject the aP immunogenic composition of claim 1.

14. A method of protecting a subject from whooping cough caused by infection with a PRN-negative strain of *Bordetella pertussis*, the method comprising:
   administering to the subject the aP immunogenic composition of claim 1.

15. A method of vaccinating a human subject against *Bordetella pertussis*, the method comprising:
   administering to the subject the following *B. pertussis* antigens: *pertussis* toxoid (PT), filamentous hemagglutinin (FHA), and unconjugated fimbriae types 2 and 3 (FIM),
   wherein FIM is administered in an amount consisting of 12-100 μg FIM.

16. The method according to claim 15, wherein the *B. pertussis* is a PRN-negative strain of *B. pertussis*.

17. A method of vaccinating a human subject against *Bordetella pertussis*, the method comprising:
   administering to the subject the following *B. pertussis* antigens: *pertussis* toxoid (PT), filamentous hemagglutinin (FHA), unconjugated fimbriae types 2 and 3 (FIM), and pertactin (PRN),
   wherein FIM is administered in an amount consisting of 12-100 μg FIM.

18. The method according to claim 17, wherein the *B. pertussis* is a PRN-negative strain of *B. pertussis*.

19. The aP immunogenic composition of claim 5, further comprising: pertactin.

20. The aP immunogenic composition of claim 19, further comprising:
   antigen from tetanus toxoid and diphtheria toxoid,
   adjuvant comprising aluminum hydroxide and/or aluminum phosphate, and
   one or more of:
      *Haemophilus influenzae* oligosaccharide or polysaccharide conjugate,
      hepatitis B virus surface antigen, and
      inactivated polio virus.

21. An acellular *pertussis* (aP) immunogenic composition comprising:
   *Bordetella pertussis pertussis* toxoid (PT),
   filamentous hemagglutinin (FHA), and
   unconjugated fimbriae types 2 and 3 (FIM),
wherein FIM is present in the composition in an amount consisting of 12-100 μg FIM per human dose.

22. The method according to claim 15, wherein FIM is administered in an amount consisting of 15-60 μg FIM.

23. The method according to claim 15, wherein FIM is administered in an amount consisting of 20-60 μg FIM.

24. The method according to claim 15, wherein FIM is administered in an amount consisting of 20-50 μg FIM.

25. The method according to claim 15, wherein FIM is administered in an amount consisting of 20-25 μg FIM.

* * * * *